(12) United States Patent
Coszach et al.

(10) Patent No.: US 8,481,675 B2
(45) Date of Patent: Jul. 9, 2013

(54) CHEMICAL RECYCLING OF PLA BY ALCOHOLYSIS

(75) Inventors: Philippe Coszach, Escanaffles (BE); Jean-Christophe Bogaert, Escanaffles (BE); Jonathan Willocq, Saint-Sauveur (ES)

(73) Assignee: Galactic S.A., Escanaffles (BE)

( * ) Notice: Subject to any disclaimer, the term of this patent is extended or adjusted under 35 U.S.C. 154(b) by 0 days.

(21) Appl. No.: 13/263,191

(22) PCT Filed: Mar. 31, 2010

(86) PCT No.: PCT/EP2010/054280
§ 371 (c)(1),
(2), (4) Date: Oct. 6, 2011

(87) PCT Pub. No.: WO2010/118955
PCT Pub. Date: Oct. 21, 2010

(65) Prior Publication Data
US 2012/0029228 A1    Feb. 2, 2012

(30) Foreign Application Priority Data

Apr. 14, 2009    (BE) .................................. 2009/0231

(51) Int. Cl.
*C08G 64/00*    (2006.01)
*C08G 63/02*    (2006.01)
(52) U.S. Cl.
USPC ........ 528/480; 528/308.1; 528/345; 528/500; 562/170; 562/580; 562/589

(58) Field of Classification Search
USPC ............... 528/308.1, 345, 480, 500; 562/170, 562/179, 580, 589
See application file for complete search history.

(56) References Cited

U.S. PATENT DOCUMENTS

| | | | |
|---|---|---|---|
| 5,229,528 A | 7/1993 | Brake et al. | |
| 5,264,614 A | 11/1993 | Brake | |
| 5,264,617 A | 11/1993 | Brake | |
| 2011/0160480 A1 | 6/2011 | Hottois et al. | |
| 2012/0142958 A1* | 6/2012 | Coszach et al. ............... | 560/179 |

FOREIGN PATENT DOCUMENTS

| | | |
|---|---|---|
| BE | 1017951 A3 | 1/2010 |
| EP | 0628533 A1 | 12/1994 |

OTHER PUBLICATIONS

International Search Report completed by the EP Searching Authority on May 21, 2010 in connection with PCT/EP2010/054280 (French text).
International Search Report completed by the EP Searching Authority on May 21, 2010 in connection with PCT/EP2010/054280 (English translation).
F.D. Kopinke, et al. "Thermal decomposition of biodegradable polyesters—II. Poly (lactic acid)", Polymer Degradation and Stability, vol. 53, 329-342, 1996.

* cited by examiner

*Primary Examiner* — Terressa Boykin
(74) *Attorney, Agent, or Firm* — Reichel IP LLP; Kevin R. Erdman; Mark C. Reichel

(57) ABSTRACT

A process for recycling a polymer blend necessarily containing PLA, comprising grinding, compacting, dissolving in a solvent of PLA, removing the undissolved contamining polymers, alcoholysis depolymerisation reaction and purification steps.

24 Claims, No Drawings

CHEMICAL RECYCLING OF PLA BY ALCOHOLYSIS

CROSS-REFERENCE TO RELATED APPLICATIONS

This application is the U. S. national phase of PCT/EP2010/054280 filed Mar. 31, 2010, the disclosure of which is incorporated by reference herein. PCT/EP2010/054280 claims the benefit under the Convention of Belgian Patent Application No. 2009/0231 filed Apr. 14, 2009, the disclosure of which is incorporated by reference herein.

FIELD OF THE INVENTION

The present invention relates to a process of chemical recycling also called depolymerisation of polylactide (PLA), whether contained or not in a blend of other polymers, for reforming the monomer or a derivative thereof.

Nowadays, in order to promote the extension of biopolymers, the use of which comes within the environment safety perspective, it is essential to be able to demonstrate the viability of management of the end-of-life of these products. The object of the present invention is to meet these issues in the case of polylactide (PLA) by providing an original solution different from the already existing ones.

STATE OF THE ART

The management of the end-of-life of plastic materials is a very important factor of the viability of a plastic material available on the market (for example, PVC has been taken off the market of plastic bottles for lack of an effective recycling system). Like non-renewable plastics (from petrochemistry) and even though their end-of-life channels are more numerous, biopolymers face technical challenges as far as this management of end-of-life is concerned. In particular, when very huge volumes are at stake, which are generated in goods market. It is the reason why it is important to address this problem.

Currently, different ways enabling to manage the end-of-life waste are already known such as dumping, incineration, composting, mechanical recycling or chemical recycling.

For the dumping, it has been seen that pollutants, mainly methane and carbon dioxide, but also pesticides, heavy metals and additives, are emitted upon degrading in a dump. If dumping waste has long been a practical and cheap solution, it has been observed, besides the above-mentioned pollutant emissions, that waste go on degrading producing leachates and gases which must continue to be discharged and processed for periods up to several tens of years. In the case of biopolymers, however, the pollution is less important since degradation products are less toxic. Nevertheless, the degradation duration sometimes long enough should be taken into consideration, which may be an issue when volumes to be processed are important.

The object of this invention is to reduce the waste volume by converting it into gases ($CO_2$, $H_2O$, $SO_x$, HCl, $NO_x$, ...), it is therefore unavoidable that the air composition in the vicinity of incinerators be altered and contains higher levels of toxic substances. In the case of bioplastics, $CO_2$ rejections are less of an issue because carbon is not a fossil origin, therefore the overall balance is neutral, or even slightly positive taking account of emissions due to the process (biomass towards bioplastics). On the contrary, other rejections are much of an issue and consequently unavoidably result in an altered air composition. If well designed and well operated, incinerators could reduce emissions thereof but this technology is extremely costly both in terms of investments and expenditures. However, incineration provides an alternative to dumping and enables producing energy, indeed, a boiler can recover heat and valorise it, possibly as electrical and thermal energy (cogeneration). Since incinerators were important sources of pollution in the past, they were called "thermal valorisation centres" and then "energy valorisation plants" in lieu of "incineration plants". However, files for implanting new units are increasingly complex to be managed because people who live in the surroundings do not accept to have an incinerator in the vicinity of their home any longer.

Biodegrability, an important property of biopolymers, can be advantageously valorised by composting which does not impact environment when necessary precautions are taken, nevertheless, the evolution of the start material to final stage depends on a great number of external factors (material dimensions, humidity rate, ventilation, pH, bacterial flora, carbon-nitrogen ratio, ... ) sometimes restricting its use. Moreover, the difficulty in identifying and sorting products containing biodegradable polymers (food packages, bags, ... ) may deteriorate the compost quality in the case a mistake upon sorting is made. Besides, improving PLA quality (better thermal resistance, better mechanical properties, ... ) results in a slower degradation.

Mechanical recycling is also known and used, for example in the case of poly(ethylene terephthalate) (PET). It consists in remelting the material, alone or in admixture with virgin material, to make marketable products. Waste is washed, dried, crystallised and ground and then directly transformed into finished products or granules which may then be marketed. This pathway is also applicable to PLA. However, since the temperatures used are high, a polymer degradation is often observed, involving a loss of its mechanical properties, both for PLA and any other polymers. The product can then be directed to less noble applications or be mixed with virgin materials. Therefore, this type of recycling is not infinite. Moreover, recycling poses problems when plastics are of different compositions since they generally are not compatible between one other. Indeed, the transformation temperatures are different and mixing several plastics results in a decrease of the quality of mechanical characteristics of the final product.

These different end-of-life techniques are not ideal because the plastic materials are not recycled into base elements (monomers) and thus directly and perpetually usable. Yet, these processes are viable for PLA but only if the material flow is exclusively comprised of PLA. Indeed, if other polymers contaminate PLA, the different above-mentioned techniques are made difficult. For example, in the case of a PET contamination, the latter is not degraded in a compost. In the case of a PVC contamination, incineration is possible but involves using costly filters due to noxious releases. Regarding chemical recycling, the obtained product is completely denatured if it is comprised of a polymer blend.

Another recycling pathway is also known as chemical recycling. Often quoted as the ideal recycling pathway, it consists in transforming the polymer by a chemical process such as for example: thermal or catalytic cracking into hydrocarbons, pyrolysis which converts back to monomers, .... A chemical recycling system for PET is known, that is depolymerisation thereof by a diol, also called glycolysis. The molecular chain is broken and the obtained products are terephthalic acid and ethylene glycol. Nevertheless, some degradation mechanisms during this depolymerisation generate irreversible structural modifications of the material, which can be responsible for difficulties in successive transformations. A PLA chemical recycling system may also be contemplated in order to recover the monomer, lactic acid or a derivative thereof. Some patents claim for example fast hydrolysis (Brake, L. D.; Subramanian, N. S. U.S. Pat. No. 5,229,528, 1993) or solvolysis (Brake, L. D. U.S. Pat. No. 5,264,614, 1993; Brake, L. D. U.S. Pat. No. 5,264,617, 1993) of a poly(hydroxy-acid) including PLA while producing hydroxy-acids or esters thereof. These known processes even enable to achieve a yield close to 95% but this involves performing a great number of steps (esterification followed by distillation, these steps being repeated three times). However, it turns out that such a handling has a serious caking risk in particular during distillation steps, which makes a transposition of the process at the industrial scale uncertain. It also turns out that dissolving the alcohol is not an easy task. Indeed, in the case of ethanol for example, it is not possible to continuously add (and thus at atmospheric pressure) PLA at a temperature higher than 78° C. (boiling point of ethanol). Due to the low density of some non densified homogenates, this results in a restricted PLA concentration. Besides, the PLA feeding the chemical recycling flow generally contains water in low amounts. This water can cause a hydrolysis of the ester formed, which can release lactic acid this way. This lactic acid production is very cumbersome in the case where the aimed quality involves a purification through distillation with rectification following solvolysis. Indeed, the distillation could not be conducted optimally, since the presence of lactic acid promotes an oligomerisation of the medium (BE Patent BE 20080424 "Procédé continu d'obtention d'un ester lactique"). Thermal degradations (for example pyrolysis) of PLA are also known, causing lactide formation (F. D. Kopinke, M. Remmler, K. Mackenzie, M. Möder, O. Wachsen, Polymer Degradation and stability, 53, 329-342, 1996) through an addition-elimination cyclization mechanism. But these methods have a low monomer yield. Moreover, these different techniques are often carried out at high temperature and/or high pressure which causes a chemical and optical degradation of the lactic acid obtained.

Therefore, there is a need for a simple, effective and non-denaturating process for depolymerising PLA in order to be able to recycle it as the basis monomer or one derivative thereof.

BRIEF DESCRIPTION OF THE INVENTION

One object of the present invention is to provide a process for the chemical recycling or depolymerisation of PLA, whether contained or not in a blend of other polymers, into lactic acid or a derivative thereof, such as a lactic acid ester, through alcoholysis, under mild conditions, by producing monomers with high quality and high yield, by increasing productivity, by decreasing $CO_2$ emissions and reducing the energy cost.

Another object of the invention is to dissolve PLA in a PLA solvent which does not block its depolymerisation and which does not impose further purification steps.

One further object of the present invention is to provide a process for the chemical recycling of a polymer blend necessarily containing PLA, wherein the blend is dissolved in a solvent for PLA to first separate the solid impurities such as polymers other than PLA which are not dissolved, and then the PLA solution is subjected to alcoholysis in order to transform PLA into the monomer or a derivative thereof.

One object of the process of the present invention is also to use as a solvent for dissolving PLA, a lactic ester so as to highly simplify the process, as well as having a positive impact on all the steps of the process for the chemical recycling of polylactic acid.

DETAILED DESCRIPTION OF THE INVENTION

The applicant has found that performing such a depolymerisation process could be remarkably improved if dissolving PLA or a polymer blend containing PLA in a lactic ester was carried out beforehand.

The process of the invention comprises consecutively the following steps; first grinding PLA or a polymer blend containing PLA is carried out, a lactic ester is used for dissolving PLA and simultaneously separating solid impurities such as polymers other than PLA which are undissolved, and then the solution thus obtained is subjected to a depolymerisation through alcoholysis and finally the lactic acid or a derivative thereof obtained is purified so as to obtain products meeting specific demands of the conventional market such as industrial applications or even PLA polymerisation.

1. Grinding the PLA Waste

Within the scope of the present invention, the raw materials used during this chemical recycling may come from out of specification products in production units, production trimmings in transformation units as well as finished products at the end of their life. First, grinding PLA or a polymer blend containing PLA is carried out according to either technique known to those skilled in the art, as for example shearing, impact, dry or water grinding. Since the object of this step is to increase the specific surface area of materials, so as to obtain a weight/volume ratio between 0.05 and 1.4 $t/m^3$, which enables to make handling steps easier and speed up the following dissolving step, making the process more easily industrializable. Within the scope of the invention, one or more grinding steps can be contemplated, their number depending on the starting product but also on the cost of these operations and the targeted final granulation. It is also possible to pre- or post-process PLA flows or polymer blend containing PLA in particular by proceeding to a washing with water or other solutions such as for example soda, potash or detergent solution, . . . . Other conducting, such as manual sorting or an automatic (for example magnetic) separation can be contemplated, all this for the purpose of remove possible waste which could alter the quality of the final product or complicate purification thereof. It is also obvious that if the waste from PLA or the polymer blend containing PLA to be processed have a suitable surface area to start dissolving, this grinding step may be suppressed without departing from the process of the present invention.

Following this grinding step, when performed, a densification step may be contemplated in order to compact the material, which would improve the handling and logistics steps.

2. Dissolving PLA or the Polymer Blend Containing Ground PLA

Then, the polymer blend containing PLA, whether ground or not, and compacted or not, is dissolved prior to the depolymerisation step. The dissolving can also be carried out without prior grinding if the form of PLA or the polymer blend containing PLA (weight/volume ratio) permits it. Indeed, one of the problems for processing this type of flow is the difference in specific mass of the different reprocessed materials event after the grinding step. Even though it is known that a main advantage of this dissolving is to remove the problem of the low density of the material to be processed (even when an identification step is carried out), thus resulting in an improved productivity per volume unit. Furthermore, the solvent used must not be cumbersome for subsequent steps.

First, this enables to easily separate the polymers other than PLA and to recover them for a specific, separated and subsequent processing.

Surprisingly, it has now be found that by carrying out this dissolving of PLA in a lactic acid ester, the further subsequent separation step could be avoided without decreasing the recycled or depolymerised material yield. These are esters such as methyl lactate, ethyl lactate, isopropyl lactate, butyl lactate, hexyl lactate, . . . and more generally a lactic acid alkyl ester, the alkyl radical of which has from 1 to 12 carbon atoms. It has also been found that dissolving lactic ester has the advantage to be able to be carried out at higher temperatures than those reached during the solubilisation in the alcohol this ester is derived of. Indeed, the boiling temperature of the ester is generally higher than that of the alcohol, which enables dissolving more PLA. Moreover, this dissolving is fast enough and can be carried out in a few minutes.

The applicant has now found that it is possible through this handling to double the PLA volume capacity and thus the amount of processed material. This dissolving may be prior or simultaneous to the following step and carried out at different temperatures up to the PLA melting temperature. The applicant company has also highlighted that it is possible to remove the water present in PLA during this dissolving step. Indeed, in view of the boiling temperature of the lactic acid esters recommended in the process of the present invention, dissolving can be carried out at a temperature higher than 100° C. and at atmospheric pressure, water can be easily removed through condensation. In the case of a PLA flow contamination by another polymer (PET, PE, PVC, PP or any other common polymers), it is possible to remove the latter through filtration if necessary while hot or any other means known to those skilled in the art.

Indeed, lactic esters do no enable dissolving the above-mentioned polymers for the required processing times.

3. The Chemical Recycling of PLA

After this dissolving, the following step consists in depolymerising PLA in order to convert it back to its basis monomer (lactic acid) or one derivative thereof. It is preferable to carry out this operation under sufficiently mild conditions to avoid a degradation of the lactic acid or one derivative thereof. Providing dissolved PLA enables the imperative obligation to exceed its melting temperature to be avoided and thus due to milder conditions, the degradation reactions to be reduced and thus to allow for obtaining a yield close to 100%.

The applicant company has also shown that PLA depolymerisation could be made through alcoholysis at a temperature between 80 and 180° C., preferably between 110 and 160° C., and more preferably between 120 and 140° C., under depression or at a pressure between the atmospheric pressure and 10 bars or higher. This PLA alcoholysis step enables to produce a lactic acid ester by breaking down an ester linkage of the polylactide followed by a protonation of the carbonyl group and a nucleophilic attack. The protonation of the carbonyl group is carried out through the use of a transesterification catalyst, which may be solid or liquid and of Lewis acid type such as for example tin octoate, tin lactate, antimony octoate, zinc octoate, APTS (paratoluenesulfonic acid), etc. or preferably basic, a member of the guanidine family, such as for example TBD (triazabicyclodecene) and derivatives thereof. Regarding the nucleophilic attack, it is carried out using an alcohol. Since the amount of alcohol influences reaction kinetics, it is nevertheless important to hold a compromise enabling to avoid removing a too high amount of alcohol during the following purification steps. Within the scope of this invention, may be used alcohols containing from 1 to 12 carbons, ideally corresponding to the ester used for dissolving, such as methanol, ethanol, n-butanol, isobutanol, sec-butanol, tert-butanol, n-propanol, isopropanol, 2-ethylhexanol, 2-ethylbutanol, hexanol, . . . . It is also possible de remove water present in PLA during this alcoholysis step, through processing the reflux. Using a Dean-Stark type system can even be recommended for a removal through forming heterogeneous azeotrope between water and alcohol. It may also be useful to replenish the alcohol if water is removed through forming an homogeneous azeotrope. The contaminated alcohol can be processed by any technique known to those skilled in the art, such as for example molecular sieves, pervaporation, . . . .

One of the particular embodiments of this invention is the dissolving in the lactic ester during which the humidity potentially present in PLA is removed through evaporation in order to avoid a hydrolysis of the lactic esters that will be formed. The lactic acid release and the oligomerisation catalysed by the same molecule are thus avoided.

A preferred embodiment of this invention is the dissolving in lactic ester during which the humidity potentially present in PLA is removed through evaporation. The alcoholysis reaction is then carried out on the water-free solution in the presence of a basic catalyst in order to suppress any problems related to acidity during the subsequent steps of the process.

4. The Purification of the Lactic Acid Ester Formed through Alcoholysis

This part of the invention consists in purifying the lactic acid ester obtained during PLA alcoholysis, since the product purity may be variable depending on the use being aimed at. It is possible to achieve high quality grades meeting market criteria. Any purification technique can be contemplated such as for example solid/liquid separations, distillation (rectification, . . . ), crystallization, extraction, passing through resins or any other methods known to those skilled in the art enabling thermosensitive molecules to be processed.

5. The Hydrolysis of the Lactic Acid Ester

In this invention, it can also be contemplated to hydrolyse the lactic acid ester, obtained during the alcoholysis, into lactic acid. After the purification step, the lactic acid ester is recovered in order to be hydrolysed. It is then blended with water in the presence or the absence of the catalyst, whether or not bonded on a resin. Preferably, this will be bonded. The amount of water recommended will be minimum for a maximum yield, in order to decrease the energy expenditure during the concentration of the lactic acid obtained. This hydrolysis can be carried out at atmospheric pressure or under depression, it can also be conducted in a batch or continuous manner by any method known to those skilled in the art such as reactive distillation, use of a piston flow reactor, . . . . The reaction is:

Lactic acid ester+water ⇔ lactic acid+alcohol

It is necessary to carry out the extraction of alcohol in order to shift the equilibrium of the reaction towards the formation of lactic acid.

The recovered lactic acid meets specifications of industrial applications or other from the market. In some cases, it could be used for reforming PLA.

Other details and particularities of the invention, given herein below by way of non-limiting examples, appear more clearly from the description as some possible embodiments.

EXAMPLE 1

Recycling PLA Cups by Dissolving in Lactic Ester Followed by an Alcoholysis 1.500 kg of used PLA cups have been ground using a knife grinder. This step allowed to increase the density of the volume to be processed, indeed the latter changed from 0.14 to 0.25 kg/l. This homogenate is then dissolved in 1.000 kg of LEt at a temperature of 130° C. under stirring. The end of dissolving is observed 5 minutes after the last addition. In order to remove the water potentially present in the PLA flow, stirring at 130° C. and at atmospheric pressure has been continued for 30 minutes. In total, 11 ml of water have been recovered through condensation.

The obtained solution has then been transferred in a vitrified reactor enabling working under pressure. 1.917 kg of ethanol are then added as well as 15 g of TBD. The depolymerisation reaction has then been conducted between 2.6 and 2.8 bars. Since the maximum temperature obtained is 138° C., this temperature lower than the PLA melting point enables a degradation of the product to be avoided. Once the reaction has ended, the product has been analysed. The results are set out in Table 1.

TABLE 1

Characteristics of the PLA alcoholysate

| $H_2O$ [a] (%) | LEt [b] (%) | EtOH [b] (%) | Lactic acid [c] (%) |
|---|---|---|---|
| 0.08 | 78.2 | 21.6 | 0.09 |

[a] determined by Karl Fischer measurement
[b] determined by ethyl lactate GC
[c] determined by titration The reaction product has then been purified by batch distillation. During this distillation, two steps have been observed:
  phase 1: recovering ethanol at the column head
  phase 2: recovering ethyl lactate (being described in Table 2)

Almost the entire solution has been distilled. The distillation residue only represents 2% of the total weight involved and is mainly comprised of paint residues, stains and other impurities.

TABLE 2

Characteristics of the ethyl lactate phase (phase 2)

| $H_2O$ [a] (%) | LEt [b] (%) | EtOH [b] (%) | Lactic acid (%) |
|---|---|---|---|
| 0.11 | 99.8 | N.D. | 0.07 |

[a] determined by Karl Fischer measurement
[b] determined by ethyl lactate GC
[c] determined by titration This way of performing enables in a single reaction step and a simple purification, to recover 98% of the expected ethyl lactate (dissolving solvent and reaction product), representing a recovery yield of LEt coming from the depolymerisation reaction of about 97%.

EXAMPLE 2

Dissolving in a Lactic Ester

Within the scope of this example, ground PLA has been dissolved in different lactic acid esters, that is methyl lactate, ethyl lactate and n-butyl lactate, in an oven at 130° C., at atmospheric pressure and without stirring. The results of these dissolvings are set out in Table 3.

TABLE 3

Dissolving PLA in different lactic acid esters

| test | Ester | PLA/ester mass ratio | time (hr) | Complete dissolving |
|---|---|---|---|---|
| 1 | methyl L | 1 | 1.5 | yes |
| 2 | ethyl L | 1 | 2 | yes |
| 3 | n-butyl L | 1 | 3 | yes |

The solubilisation at atmospheric pressure of PLA in the lactic esters or their respective alcohols has been compared in the following example.

TABLE 4

Comparison of the dissolvings of PLA in lactic esters or their respective alcohols

| test | Solvent | PLA/ester mass ratio | Temp. (° C.) | time (hr) | Complete dissolving |
|---|---|---|---|---|---|
| 1 | Ethanol | 1 | 78° C. | 3 | no |
| 2 | ethyl L | 1 | 120° C. | 3 | yes |
| 3 | n-butanol | 1 | 120° C. | 3 | no |
| 4 | n-butyl L | 1 | 120° C. | 3 | yes |

In the case of ethyl lactate, different ester/PLA ratios and different temperatures have been studied and compared after a 4 hrs duration without stirring at atmospheric pressure. The results are set out in Table 5.

TABLE 5

Dissolving in ethyl lactate of ground PLA in different proportions

| test | PLA/LEt mass ratio | t (° C.) | Dissolving at |
|---|---|---|---|
| 1 | 0.75 | 130 | 100% |
| 2 | 1 | 130 | 100% |
| 3 | 1.5 | 130 | 100% |
| 4 | 2 | 130 | 100% |
| 5 | 1 | 120 | 100% |
| 6 | 1.25 | 120 | 100% |
| 7 | 1.5 | 120 | 100% |
| 8 | 1.75 | 120 | ~85% |
| 9 | 2 | 120 | ~75% |

Tests 8 and 9 have been continued for 2 further hours. The entire PLA test 8 is dissolved. Conversely, 10% of the PLA from test 9 have not been dissolved.

A dissolving of ground fibres (density=0.22) has been carried out under conditions close to industrial ones (stirring, higher quantities of material, at atmospheric pressure, . . . ). 1.5 kg of PLA has been dissolved in 1 kg of ethyl lactate at 130° C. The end of dissolving is observed 5 minutes after the last addition. The obtained solution had a density of about 1.25.

It also has been attempted to dissolve different polymers likely to be able to contaminate the PLA flow, in ethyl lactate, at 130° C., at atmospheric pressure, for 4 hrs and without stirring. The results are set out in Table 6.

TABLE 6

Dissolving in ethyl lactate of different ground polymers

| Polymer | Polymer/LEt mass ratio | Dissolving | Appearance of the blend |
|---|---|---|---|
| PEHD | 1 | no | suspension |
| PP | 0.14 | no | suspension |
| PET | 0.37 | no | suspension |
| PLA* | 1 | yes | solution |

*given by way of comparative example

The previous example seems to prove that separating polymers contaminating the PLA by dissolving in a lactic acid ester is possible. For this to be confirmed, dissolvings in ethyl lactate, of PLA contaminated by one of these polymers (10%) have been carried out at 130° C., for 4 hrs and without stirring (polymer/LEt mass ratio=0.5). The insolubles are then recovered by filtration, and then thoroughly washed with water, dried and weighed. The results are set out in Table 7. The slight differences in masses before and after dissolving attempt are due to the accuracy of the method being used.

TABLE 7

Dissolving in ethyl lactate of PLA contaminated by another polymer

| Test | Polymer tested | Amount of contaminant before dissolving | Amount of contaminant recovered |
|---|---|---|---|
| 1 | PEHD | 2.03 g | 2.04 g |
| 2 | PP | 1.99 g | 1.99 g |
| 3 | PET | 2.04 g | 2.03 g |

EXAMPLE 3

Dissolving in n-butyl Lactate, Followed by an Alcoholysis Reaction with n-butanol 600 g of ground and dried PLA have been dissolved in 600 g of n-butyl lactate. The dissolving has been carried out in a 3 litre flask at ambient pressure and at 130° C. In order to mimic a PLA flow containing a little of water, 30 g of water have been further added. To the obtained solution have been added 1233 g of n-butanol and 6 g of TBD in order to conduct the alcoholysis reaction (butanol/PLA molar ratio: 2). The reaction has been conducted for 20 hrs at ambient pressure and at 120° C. (temperature sufficient to solubilise PLA in the ester and being mild, which enables a degradation of the product to be avoided). During the reaction, water is removed through condensation of the heterogeneous azeotrope formed by water and butanol. The butanol phase is reinjected in the flask using a Dean-Stark type system. The alcoholysis result has then been analysed and the results are set out in Table 8.

TABLE 8

Characteristics of the reaction product

| Water [a] (%) | LBut [b] (%) | Butanol [b] (%) | Lactic acid [c] (%) |
|---|---|---|---|
| 0.05 | 74.6 | 25.3 | 0.07 |

[a] determined by Karl Fischer measurement
[b] determined by butyl lactate GC
[c] determined by titration The reaction product has then been distilled in order to recover the butyl lactate being formed. The distillation has very well progressed due to the very low water and acid concentration in the reaction product. The ethyl lactate phase has been analysed and the results are described in Table 9.

TABLE 9

Characteristics of the butyl lactate phase

| Water [a] (%) | LBut [b] (%) | Butanol [b] (%) | Lactic acid [c] (%) |
|---|---|---|---|
| 0.17 | 99.7 | N.D. | 0.09 |

[a] determined by Karl Fischer measurement
[b] determined by butyl lactate GC
[c] determined by titration This way of performing enables in a single reaction step and a simple purification to recover more than 97% of the butyl lactate (dissolving solvent and reaction product), representing a recovery yield of the lactic ester coming from the depolymerisation reaction of about 96%.

EXAMPLE 4

Dissolving a Ground PLA in Ethyl Lactate without Removing Water Followed by the Alcoholysis Reaction in the Presence of Ethanol In a vitrified reactor are placed 1.204 kg of ground used PLA cups dissolved beforehand under reflux in 1.4 kg of ethyl lactate. Then 1.538 kg of ethanol as well as 12 g of TBD are further added to the dissolved PLA. This content is then heated during 24 hrs, so as to obtain a pressure between 2.6 and 2.8 bars. Since the maximum temperature obtained is 138° C., this temperature lower than the PLA melting temperature enables a degradation of the product to be avoided. Once the reaction has ended, the product has been analysed. The results are set out in Table 10. It is clearly seen that the resulting water and lactic acid contents are significantly higher than those observed in Example 1.

TABLE 10

Characteristics of the alcoholysate of PLA fibres

| $H_2O$ [a] (%) | LEt [b] (%) | EtOH [b] (%) | Lactic acid [c] (%) |
|---|---|---|---|
| 0.62 | 80.7 | 17.7 | 0.96 |

[a] determined by Karl Fischer measurement
[b] determined by ethyl lactate GC
[c] determined by titration The reaction product has then been distilled. During this distillation, three phases have been observed, the first one being the ethanol recovering at the column head. Then, ethyl lactate has been obtained. This phase has, in a third step, been disturbed by an oligomerisation releasing volatiles, thus preventing from recovering pure ethyl lactate. The ethyl lactate phase has been analysed, the results are set out in Table 11.

TABLE 11

| Characteristics of the ethyl lactate phase (phase 2) | | | |
|---|---|---|---|
| $H_2O$ [a] (%) | LEt [b] (%) | EtOH [b] (%) | Lactic acid (%) |
| 0.10 | 99.8 | N.D. | 0.07 |

[a] determined by Karl Fischer measurement
[b] determined by ethyl lactate GC
[c] determined by titration This way of performing enables us to recover only 61% of the ethyl lactate theoretically contemplated. This example shows the importance to control the humidity likely to be present in PLA.

EXAMPLE 5

Hydrolysis of the Ester into Lactic Acid

The butyl lactate obtained in Example 4 has been hydrolysed in order to recover lactic acid therefrom. To do this, 500 g of the butyl lactate phase obtained have been placed in a 1 litre flask with 123 g of water (water/LBut molar ratio: 2). The reaction has been conducted at 105° C. and at atmospheric pressure. In order to drive the reaction to the lactic acid release, the released alcohol is removed through condensation of the heterogeneous azeotrope formed by water and butanol. Water is separated from butanol with a Dean-Stark and reinjected in the reaction flask. Almost the entire butyl lactate is hydrolysed after 20 hours. The obtained product meets quality criteria from the market. The results are set out in Table 12.

TABLE 12

| Characteristics of the hydrolysate after filtration | | | |
|---|---|---|---|
| $H_2O$ [a] (%) | LBut [b] (%) | Butanol [b] (%) | Lactic acid [c] (%) |
| 16.7 | 0.09 | Not detected | 83.2 |

[a] determined by Karl Fischer measurement
[b] determine by butyl lactate GC
[c] determined by titration

EXAMPLE 6

Dissolving a Ground PLA Contaminated with Poly(Ethylene Terephthalate) (2%) in Ethyl Lactate Followed by the Alcoholysis Reaction in the Presence of Ethanol—Removal of the Contaminant After Dissolving 1.204 kg of ground used PLA cups have been contaminated with 2% of poly(ethylene terephthalate), that is 24 g. The blend has then been dissolved in 1.4 kg of ethyl lactate at 130° C., at atmospheric pressure and under stirring. The end of dissolving has been observed 5 minutes after the last addition. In order to remove water potentially present in the PLA flow, stirring at 130° C. and at atmospheric pressure has been continued for 30 minutes. In total, 9 ml of water have been recovered through condensation. The solution has then been filtered while hot in order to recover the undissolved PET. This operation enabled us to recover the entire contaminating polymer (that is 24 g).

The filtrate has been transferred in a vitrified reactor enabling working under pressure. 1.538 kg of ethanol have then been added as well as 12 g of TBD.

The depolymerisation reaction has then been conducted between 2.6 and 2.8 bars. Since the maximum temperature obtained is 136° C., this temperature lower than PLA melting temperatures enables a degradation of the product to be avoided. Once the reaction has ended, the product has been analysed. The results are set out in Table 13.

TABLE 13

| Characteristics of the filtrate | | | |
|---|---|---|---|
| $H_2O$ [a] (%) | LEt [b] (%) | EtOH [b] (%) | Lactic acid [c] (%) |
| 0.11 | 80.9 | 18.9 | 0.07 |

[a] determined by Karl Fischer measurement
[b] determined by ethyl lactate GC
[c] determined by titration

EXAMPLE 7

Dissolving Ground PLA Contaminated with Poly(Propylene) (1%) in Ethyl Lactate Followed by an Alcoholysis Reaction in the Presence of Ethanol—Removal of the Contaminant after Reaction 1.204 kg of ground used PLA cups have been contaminated with 1% of poly(propylene), that is 12 g. The blend has then been dissolved in 1.4 kg of ethyl lactate at 130° C., at atmospheric pressure and under stirring. The end of dissolving has been observed 5 minutes after the last addition. In order to remove water potentially present in the PLA flow, stirring at 130° C. and at atmospheric pressure has been continued for 30 minutes. In total, 10 ml of water have been recovered through condensation.

The obtained solution has then been transferred into a vitrified reactor enabling working under pressure. 1.538 kg of ethanol have then been added as well as 12 g of TBD.

The depolymerisation reaction has then been conducted between 2.6 and 2.8 bars. Since the maximum temperature obtained is 137° C., this temperature lower than PLA and PP melting temperatures enables a degradation of the product to be avoided. Once the reaction has ended, the alcoholysis result has been filtered in order to recover the contaminating polymer. The 12 g of PP initially introduced into the reactor have thus been recovered. The filtrate has been analysed, and the results are set out in Table 14.

TABLE 14

| Characteristics of the filtrate | | | |
|---|---|---|---|
| $H_2O$ [a] (%) | LEt [b] (%) | EtOH [b] (%) | Lactic acid [c] (%) |
| 0.12 | 81.2 | 18.6 | 0.09 |

[a] determined by Karl Fischer measurement
[b] determined by ethyl lactate GC
[c] determined by titration

The invention claimed is:
1. A process for recycling a polymer blend comprising PLA, characterised in that it comprises the steps of:

a) dissolving the ground and/or compacted polymer blend in a solvent of PLA in order to separate PLA from the other polymers;
b) recovering undissolved polymers for separate and subsequent processing;
c) recovering the PLA solution with a weight ratio PLA/solvent between about 0.5 and about 3.0 and subjecting it to a catalytic alcoholysis reaction, at a temperature between about 80° C. and about 180° C. and a pressure between about 0.05 and about 10 bars, in order to transform PLA into lactic ester; and
d) purifying the lactic ester thus recovered.

2. The process according to claim 1 wherein said solvent of PLA is a lactic ester.

3. The process according to claim 1, characterised in that dissolving the polymer blend in a lactic ester is carried out at a temperature between the boiling temperature of water and the boiling temperature of the ester at operating pressure, for a period of time sufficient to obtain a weight ratio of PLA/lactic ester between about 0.5 and about 3.0.

4. The process according to claim 3, characterised in that the operating pressure is between about 0.05 and about 10 bars.

5. The process according to claim 2, characterised in that the lactic ester is an alkyl lactate, wherein the alkyl radical of the alkyl lactate contains from 1 to 12 carbon atoms.

6. The process according to claim 4, characterised in that the alkyl lactate is selected from the group consisting of methyl, ethyl, isopropyl, butyl or hexyl lactate.

7. The process according to claim 1, characterised in that the catalytic alcoholysis reaction is performed in the presence of a basic catalyst.

8. The process according to claim 7, characterised in that the basic catalyst is a guanidine.

9. A process for recycling PLA by depolymerising it the PLA into a monomer or a derivative thereof, comprising dissolving it PLA in a solvent, catalytically alcoholysing the dissolved PLA into a lactic ester, and purifying the lactic ester thus recovered, characterised in that dissolving PLA is performed in a lactic ester at a temperature between the boiling temperature of water and the boiling temperature of the lactic ester at the operating pressure for a period of time sufficient to obtain a weight ratio of PLA/lactic ester between about 0.5 and about 3.0.

10. The process according to claim 9, characterised in that the operating pressure is between about 0.05 and about 10 bars.

11. The process according to claim 9, characterised in that the lactic ester is an alkyl lactate, wherein the alkyl radical of the alkyl lactate contains from 1 to 12 carbon atoms.

12. The process according to claim 11, characterised in that the alkyl lactate is selected from the group consisting of methyl, ethyl, isopropyl, butyl or hexyl lactate.

13. The process according to claim 9, characterised in that the catalytic alcoholysis reaction is performed in the presence of a basic catalyst.

14. The process according to claim 13, characterised in that the basic catalyst is a guanidine.

15. The process according to claim 3, characterised in that the weight ratio of PLA/lactic ester is between about 0.75 and about 2.0.

16. The process according to claim 8, characterised in that the guanidine is triazabicyclodecene or a derivative thereof.

17. The process according to claim 9, characterized in that the weight ratio of PLA/lactic ester is between about 0.75 and about 2.0.

18. The process according to claim 14, characterised in that guanidine is triazabicyclodecene or a derivative thereof.

19. A process for recovering lactic acid, characterised in that it compromises the steps of:
a) dissolving the ground and/or compacted polymer blend in a solvent of PLA in order to separate PLA from the other polymers;
b) recovering undissolved polymers for separate and subsequent processing;
c) recovering the PLA solution with a weight ratio PLA/solvent between about 0.5 and about 3.0 and subjecting it to a catalytic alcoholysis reaction, at a temperature between about 80° C. and about 180° C. and a pressure between about 0.05 and about 10 bars, in order to transform PLA into lactic ester;
d) purifying the lactic ester thus recovered; and
e) hydrolyzing the lactic ester into lactic acid.

20. The process according to claim 19, characterised in that the hydrolyzing is performed in the presence of a catalyst.

21. The process according to claim 19, characterised in that the hydrolyzing is performed via extraction of alcohol.

22. The process according to claim 1 comprising a step of grinding and/or compacting the polymer blend until a weight/volume ratio between about 0.05 and about 1.4 $t/m^3$ is obtained, prior to dissolution.

23. The process according to claim 19 comprising a step of grinding and/or compacting the polymer blend until a weight/volume ratio between about 0.05 and about 1.4 $t/m^3$ is obtained, prior to dissolution.

24. The process according to claim 9 comprising a step of grinding and/or compacting PLA prior to dissolution of the PLA.

* * * * *